United States Patent [19]

Benson et al.

[11] Patent Number: 5,663,472
[45] Date of Patent: Sep. 2, 1997

[54] PRODUCTION OF ALKENES

[75] Inventors: Sidney W. Benson, Los Angeles; Maja A. Weissman, Santa Clarita, both of Calif.

[73] Assignee: University of Southern California, Los Angeles, Calif.

[21] Appl. No.: 385,068

[22] Filed: Feb. 7, 1995

Related U.S. Application Data

[63] Continuation of Ser. No. 190,708, Feb. 2, 1994, abandoned, which is a continuation of Ser. No. 41,533, Apr. 1, 1993, abandoned, which is a continuation of Ser. No. 621,719, Dec. 6, 1990, abandoned, which is a continuation-in-part of Ser. No. 488,451, Feb. 23, 1990, abandoned, which is a continuation of Ser. No. 133,206, Dec. 15, 1987, abandoned, which is a continuation of Ser. No. 757,585, Jul. 22, 1985, abandoned.

[51] Int. Cl.$^6$ .............................. C07C 5/327; C07C 17/00
[52] U.S. Cl. .......................... 585/641; 585/638; 585/654; 585/656; 585/657; 585/658; 570/101; 570/181; 570/216; 570/230
[58] Field of Search .............................. 585/654, 656, 585/657, 658, 638, 641; 570/101, 181, 216, 230

[56] References Cited

U.S. PATENT DOCUMENTS

| | | |
|---|---|---|
| 2,259,195 | 10/1941 | Baehr et al. . |
| 2,488,083 | 11/1949 | Gorin et al. . |
| 2,628,259 | 2/1953 | Dirstine et al. . |
| 2,838,579 | 6/1958 | Conrad et al. ........................... 585/657 |
| 2,890,253 | 6/1959 | Mullineaux et al. . |
| 3,166,601 | 1/1965 | Taylor ........................................ 585/657 |
| 3,173,962 | 3/1965 | Carroll et al. . |
| 3,207,811 | 9/1965 | Bajars . |
| 3,557,229 | 1/1971 | Riegel . |
| 3,558,735 | 1/1971 | Beard, Jr. . |
| 3,658,934 | 4/1972 | Beard, Jr. . |
| 3,702,311 | 11/1972 | Beard, Jr. . |
| 3,862,996 | 1/1975 | Beard, Jr. . |
| 4,119,670 | 10/1978 | Kroenke et al. . |
| 4,217,311 | 8/1980 | Zaidman et al. . |
| 4,300,005 | 11/1981 | Li ................................................ 570/224 |
| 4,375,569 | 3/1983 | Kroenke et al. ........................... 570/224 |
| 4,461,919 | 7/1984 | Kroenke et al. ........................... 570/224 |
| 4,467,127 | 8/1984 | Kroenke et al. ........................... 570/224 |

FOREIGN PATENT DOCUMENTS

| | | | |
|---|---|---|---|
| 2095242 | 9/1982 | United Kingdom | C07C 21/06 |
| 2095245 | 9/1982 | United Kingdom | C07C 21/06 |

*Primary Examiner*—Glenn A. Caldarola
*Assistant Examiner*—Elizabeth D. Wood

[57] ABSTRACT

A process for reacting ethane with chlorine to produce a mixture of ethylene and vinyl chloride is disclosed. The process involves the intimate mixing of ethane and chlorine in an ethane to chlorine ratio of at least about 0.9:1 at a temperature such that ethane and chlorine do not react during mixing, and heating the mixture to a temperature above about 215° C. to commence the reaction, allowing the reaction to proceed for a period of less than about 1 minute, and providing sufficient heat to the reacting mixture so that the reacted mixture will have a temperature between about 400° C. and about 800° C.

31 Claims, 5 Drawing Sheets

PRODUCTION OF ALKENES

BACKGROUND OF THE INVENTION AND PRIOR ART STATEMENT

This application is a continuation of application Ser. No. 08/190,708, filed Feb. 2, 1994, now abandoned; which was a continuation of application Ser. No. 08/041,533 filed Apr. 1, 1993, now abandoned; which was a continuation of application Ser. No. 07/621,719 filed Dec. 6, 1990, now abandoned; which was a continuation-in-part of application Ser. No. 07/488,451 filed Feb. 23, 1990, now abandoned; which was a continuation of application Ser. No. 07/133,206 filed Dec. 15, 1987, now abandoned; which was a continuation of Ser. No. 06/757,585 filed Jul. 22, 1985, now abandoned.

This invention relates to a process for making ethylene and mixtures of ethylene and vinyl chloride. More particularly, the invention relates to a novel process for making ethylene and mixtures of ethylene and vinyl chloride by the reaction of ethane with chlorine.

Ethylene is a valuable and widely used commodity. Over ten billion pounds of ethylene are consumed each year in the United States alone, to make various grades of polyethylene.

Another major use of ethylene is as the starting material for making vinyl chloride, which can then be polymerized into polyvinyl chloride (PVC).

In view of the huge quantities of ethylene consumed each year, there is substantial interest in any economical and improved method for making ethylene. At the present time, ethylene is typically made by the high temperature dehydrogenation of ethane and cracking feedstocks such as propane, butane, and naphtha. Such high temperature processes require the expenditure of substantial amounts of energy, which is expensive.

There have been a number of attempts to develop a viable process for the dehydrogenation of ethane or other lower olefinic hydrocarbons by reaction with chlorine or chlorine-containing compound at lower temperatures. As far as we know, none of these prior attempts have resulted in a commercially viable process.

Baehr (U.S. Pat. No. 2,259,195) discloses a process in which chlorine is used to dehydrogenate paraffinic and olefinic hydrocarbons having 3 to 8 carbon atoms. In this process the chlorine and the hydrocarbon are mixed and reacted in the gas phase at a temperature of 300° C. to 800° C. In Comparative Example A herein, we show that the procedure of Baehr's Example 1, when applied to ethane, would cause almost immediate coking and plugging of the system.

Gorin et al U.S. Pat. No. 2,488,083 shows a process for converting gaseous methane and natural gas to liquid hydrocarbons via alkyl halide intermediary, followed by dehydrohalogenocondensation. The separation of hydrogen chloride from other gaseous materials is shown.

Dirstine et al (U.S. Pat. No. 2,628,259) discloses a process for chlorinating ethane to produce vinylidene chloride (1,1-dichloroethylene) and vinyl chloride. This process is conducted at a temperature of 450° C. to 600° C., in the presence of a diluent gas at a chlorine to ethane molar ratio of between 1.9:1 and 3.0:1.

Conrad (U.S. Pat. No. 2,838,579) discloses a process for the chlorination of ethane to produce chloroethane products such as ethyl chloride, 1,1-dichloroethane or 1,2-dichloroethane, or higher chloroethanes if desired. The process is conducted at high pressure in a temperature range of 300° to 600° C. in the presence of a fluidized bed catalyst consisting of inorganic, carbon coated particles.

Mullineaux (U.S. Pat. No. 2,890,253) discloses the use of iodine and oxygen to dehydrogenate saturated hydrocarbons including ethane to yield unsaturated hydrocarbons. In the example showing reaction of iodine with ethane (Example VI, column 10) the amount of ethane reacted was only 40 percent.

Taylor (U.S. Pat. No. 3,166,601) discloses a process for the chlorination of ethane to produce unsaturated, chlorinated products. This process is conducted at a temperature of 600° to 900° C. in the presence of an inert diluent gas. Carroll (U.S. Pat. No. 3,173,962) discloses a process for converting alkanes containing 2 to 6 carbon atoms into olefins and chlorinated alkanes which comprises passing a mixture of an alkane, hydrogen chloride, and oxygen or oxygen-containing gas over a catalyst, at a temperature of about 300° to 650° C.

Bajars discloses (U.S. Pat. No. 3,207,811) a catalytic process for dehydrogenating aliphatic hydrocarbons of 4 to 6 carbon atoms which comprises heating an aliphatic hydrocarbon of 4 to 6 carbon atoms with oxygen, and a source of chlorine to a temperature of at least 450° C. up to 1000° C. in the presence of a catalyst.

Riegel (U.S. Pat. No. 3,557,229) discloses a catalytic process for the oxychlorination of ethane to produce vinyl chloride, along with ethyl chloride, dichloroethane, ethylene and other compounds. The reactants are ethane, hydrochloric acid and an oxygen source.

Beard (U.S. Pat. No. 3,558,735) discloses a catalytic oxydehydrogenation process for the production of ethylene in which ethane is reacted with hydrogen chloride and oxygen in the presence of a fluidized copper chloride and rare earth halide catalyst at a temperature of above 350° C. to about 650° C.

Beard discloses (U.S. Pat. Nos. 3,658,934; 3,702,311; and 3,862,996) a catalytic process for the production of ethylene which comprises reacting ethane with a halogen, in the presence of an inert gas diluent and a catalyst at a temperature of above 350° C. to about 650° C.

Kroenke et al disclose in a series of patents (U.S. Pat. Nos. 4,119,570; 4,375,569; 4,461,919; and 4,467,127) a process for the oxychlorination of ethane to produce a mixture of ethylene, ethylene dichloride, vinyl chloride, and ethyl chloride. In this process ethane, oxygen, preferably from air, and a chlorine source such as hydrogen chloride are reacted in the presence of a catalyst at a temperature from 400° C. to about 650° C.

Zaidman et al (U.S. Pat. No. 4,217,311) disclose a process for the production of vinyl chloride. In this process, a mixture of ethylene and ethane are reacted with chlorine at a temperature of between 300° C. and 550° C. The chlorine is added at several points along the reaction zone.

Li (U.S. Pat. No. 4,300,005) discloses a catalytic process for producing monohalogenated olefins and other products by the oxychlorination of 2 to 4 carbon alkanes. In the process the alkane is reacted with a hydrogen halide, and an oxygen source at a temperature of about 400° C. to 650° C. in the presence of a catalyst.

Pyke et al (British Patent Nos. 2,095,242A and 2,095,245A) disclose a catalytic process for producing vinyl chloride by reacting ethane with a chlorine source and oxygen at a temperature of 275° C. to 500° C.

SUMMARY OF THE INVENTION

In accordance with the present invention, there is provided a process for reacting ethane with chlorine to produce a mixture of ethylene and vinyl chloride. This process is characterized by a conversion of ethane per pass through the reactor of about 50% or better and a combined molar yield of ethylene and vinyl chloride of over about 80% of the ethane consumed. In conducting the process of this invention, ethane is intimately mixed with chlorine and the mixture is heated in an inert reactor to initiate the reaction. The reaction is allowed to proceed to completion, and the reacted mixture leaving the reaction zone will have a temperature of between about 600° C. and about 800° C. The ratio of ethane to chlorine is about 0.9:1 or above.

DETAILED DESCRIPTION OF THE INVENTION

The present invention provides an efficient process for the production of ethylene or a mixture of ethylene and vinyl chloride by reacting chlorine with ethane.

In accordance with this invention, there is provided a process for preparing ethylene and vinyl chloride by the reaction of ethane and chlorine which comprises:

(a) intimately mixing ethane with chlorine to form a mixture, having a molar ratio of ethane to chlorine of at least about 0.9:1, and having a temperature such that substantially no chemical reaction takes place during said mixing;

(b) passing the mixture into an inert reaction zone;

(c) heating the mixture in the reaction zone to initiate chemical reactions to produce ethylene and vinyl chloride; and (d) permitting the reaction to proceed to completion, so that the reacted mixture leaving the reaction zone will have a temperature of from about 400° C. to about 800° C.;

whereby the combined molar yield of ethylene and vinyl chloride is at least about 80% of the ethane consumed.

It is believed that the conversion of ethane and chlorine to produce ethylene and vinyl chloride results from a series of several intermediate reactions, including:

(1) chlorination of ethane to form ethyl chloride as represented by the equation:

$$C_2H_6 + Cl_2 \rightarrow C_2H_5Cl + HCl$$

(2) cracking of ethyl chloride to form ethylene as represented by the equation:

$$C_2H_5Cl \rightarrow C_2H_4 + HCl$$

(3) chlorination and dehydrogenation of ethane to form vinyl chloride through a series of reactions which can be represented by the overall equation:

$$C_2H_6 + 2Cl_2 \rightarrow C_2H_3Cl + 3HCl$$

(4) dehydrogenation of ethane to form ethylene, as represented by the equation:

$$C_2H_6 \rightarrow C_2H_4 + H_2$$

Of these reactions, the chlorination of ethane (reaction (1)) is highly exothermic, generating 28.65 kcal/mole of ethyl chloride formed. The heat of reaction may be relied on, at least in part, in the process of this invention to heat the mixture of ethane and chlorine to the desired reaction temperature. Reaction (3) is also exothermic, generating 41 kcal/mole of vinyl chloride formed, and may also provide heat to sustain the process of this invention. Reactions (2) and (4), on the other hand, are endothermic, and require 17.27 kcal/mole of ethyl chloride reacted, and 32.74 kcal/mole of ethane reacted, respectively.

According to the present invention, ethane is mixed with gaseous chlorine at a temperature such that the two gases do not react. It is believed that reaction (1) is a free radical reaction initiated by thermal dissociation of chlorine into free radicals which then initiate the chlorination of ethane. Since such free radicals are known to be formed at a temperature of at least about 215° C., the ethane and chlorine are mixed at a temperature below 215° C. Although the ethane and chlorine may be conveniently mixed at ambient temperatures, these reactants may also be mixed at somewhat higher temperatures so long as the chlorine does not exceed about 200° C. to 215° C. either before or immediately after the mixing. Thus, for example, the ethane supplied to the mixing zone may have a temperature of about 200° C. and chlorine a temperature of about 20° C., resulting in a mixture at about 180° C., due to the molar ratio of ethane and chlorine employed and their heat capacities. It is important that the chlorine be in the gaseous form and that no liquid chlorine be present, which can lead to undesirable explosions.

The ratio of chlorine to ethane in the feed mixture should be selected carefully in conducting the process of this invention. The higher the ratio of ethane to chlorine, the less vinyl chloride will be produced. If too little chlorine is used, the reaction will produce few by-products and little vinyl chloride, but will leave a large amount of ethane unreacted. Consequently, more elaborate product separation will be required to recover the ethylene and recycle the unreacted ethane. On the other hand, the presence of too much chlorine will lead to polychlorinated products, other side products, and carbon formation. We have found that good results are obtained with a mole ratio of ethane to chlorine of at least about 0.9:1, and more generally in a range of from about 1:1 to about 4:1. The preferred range of the ratio of ethane to chlorine is from about 1:1 to about 2:1, with a ratio of from about 1.3:1.0 to about 1.6:1.0 being especially preferred.

The mixing of the ethane and chlorine may be performed by any procedure which produces an intimate mixture of the gases. If mixing is incomplete when the gas mixture is conducted to the reactor, undesired reactions will occur in regions where there is a local excess of chlorine, which can lead to the formation of polychlorinated compounds, acetylene, and even carbon. We have found that passing the gases through a packed column produces the desired mixing. However, other methods of mixing will be readily apparent to those skilled in the art.

After mixing the ethane and chlorine, the mixture is conducted to an inert reactor, where heat is added to the mixture. At about 215° C., an exothermic reaction between ethane and chlorine to produce ethyl chloride begins, and causes a further temperature rise. At approximately 600° C., the endothermic dehydrohalogenation to form ethylene occurs with some rapidity. Consequently, in order to achieve the objects of the present invention, the temperature within the reaction zone should be above about 600° C. It is preferred that the highest temperature in the reaction zone not exceed 800° C. for a substantial period of time. The temperature may exceed 800° C. if the period of high temperature is short, on the order of 1 second or so. The reaction is preferably carried out at a temperature of from about 600° C. to about 800° C., and a final temperature of the reacted mixture of from about 650° C. to about 750° C. is particularly preferred.

In order to achieve the purposes of this invention, it is important that the inner surface of the reactor be inert. Most metallic reactors cause side reactions which lead to carbon formation. We have found that quartz, silicon carbide, alumina, and graphite linings are suitable. However, one skilled in the art could, without undue experimentation, find other inert materials which would be suitable for the lining of a reactor for this process.

The inert reactor of this invention may take many forms, such as a tubular reactor, a cylindrical reactor, or a spherical reactor. It may be a single reactor or it may be divided into several reaction chambers. Each separate reaction chamber may be heated at the same rate or at different rates. The single reactor may contain regions which are heated at different rates. Optionally, the gases may pass through an unheated zone in a single reactor or an unheated chamber in a multiple chamber reactor. In this zone or chamber, the heats of reaction of the exothermic and endothermic reactions control the reaction temperature. If the reactor is a tubular reactor of a diameter small enough to cause plug flow, in the absence of heating or cooling there will be a distinct temperature profile from inlet to outlet. That is, once a reaction is initiated at about 215° C. or above, the temperature will rise due to exothermic reaction (1). Then the reaction temperature will peak and decrease as exothermic reaction (1) terminates and endothermic reactions, such as reactions (2) and (4), take place. In such a reactor, heat may be applied in the first stage to initiate the reaction and in the final stage to drive the endothermic reactions and maintain the reaction temperature in the range of 600° C. to 800° C. Reaction time is usually less than one minute. It has been found, however, that reaction times of at least 6 to 8 seconds are desired to minimize the formation of ethyl chloride.

The process of this invention is not limited to atmospheric pressure, and it may be carried out at pressures as high as about 30 atmospheres. In selecting a pressure, one must balance the greater throughput at higher pressure against the extra strength required in a high pressure reactor. It is preferred, however, to run close to atmospheric pressure, i.e., less than 2 atmospheres.

In practice, the process of this invention does not convert 100% of the ethane entering the reactor. Accordingly, the product stream from the process consists predominantly of ethylene, hydrogen chloride, some hydrogen, and unreacted ethane. The reactant gas stream may be readily fractionated, by methods well-known to those skilled in the art, to separate the various components. This is not necessary, however, and the hydrogen chloride and the ethylene may be processed together to yield 1,2-dichloroethane and vinyl chloride. In these reactions, small amounts of hydrogen and ethane do not present a problem.

Oxychlorination reactions are known, in which ethylene, hydrochloric acid and an oxygen source (generally air or pure oxygen) are reacted to form 1,2-dichloroethane. The overall equation for this reaction is:

$$C_2H_4 + 2HCl + \tfrac{1}{2}O_2 \rightarrow C_2H_4Cl_2 + H_2O$$

If the stream of product gases does not contain an appropriate balance of ethylene and hydrogen chloride, one or the other of the reactants may be added, or, alternatively, removed. Such reactions are usually conducted in a temperature range of 225° C. to 250° C. over a catalyst such as copper chloride on alumina. The product of this reaction is 1,2-dichloroethane which, in turn, may be thermally cracked to yield vinyl chloride.

Figure 5:
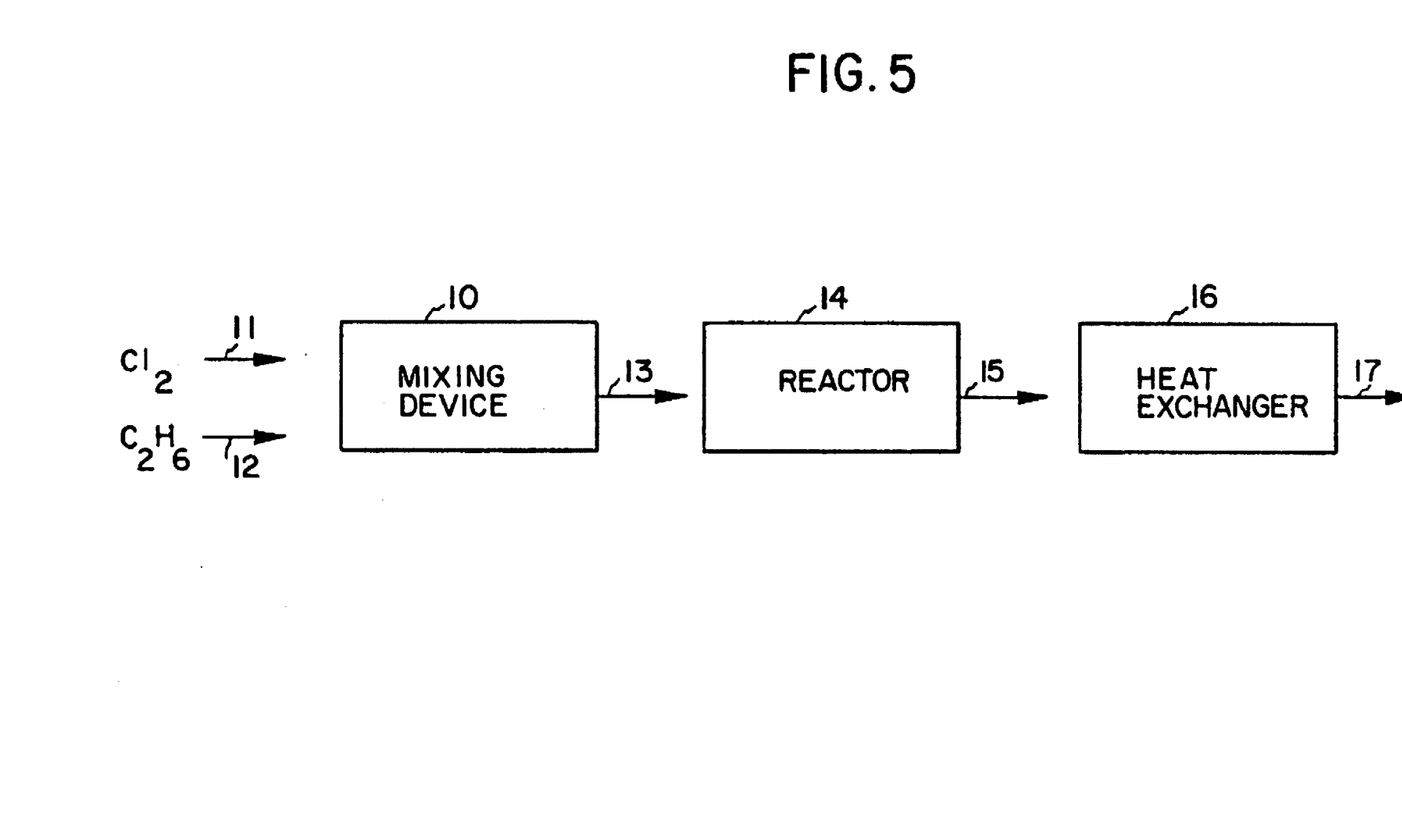
FIG. 5 is a schematic diagram of the process of the invention.

The process of the present invention is further illustrated by the schematic drawing of FIG. 5. In FIG. 5, a feed stream of chlorine 11 and a feed stream of ethane 12, which may be both at substantially ambient temperature, are fed into a mixing device 10 to produce a thoroughly mixed gaseous stream 13. Feed stream 13 is then fed into a reactor 14 equipped with heating device for raising the temperature of the mixture of chlorine and ethane to at least about 215° C. to initiate the reaction. Reactor 14 should provide sufficient heat to the reacting mixture so that the reacted mixture 15 will leave reactor 14 at about 600° C. to about 800° C. The reacted mixture 15 may then be passed through a heat exchanger 16 to quench the mixture to a cooled stream 17 for further separation and processing. As indicated above, the inner surface of reactor 14 should be inert and non-metallic, preferably made of such materials as quartz, silicon carbide, alumina or graphite linings.

The following examples, unless indicated otherwise, illustrate specific embodiments of the invention, but should be construed as merely illustrative, and not limiting of the present invention.

EXAMPLE 1

A series of experiments was performed in which mixtures of ethane and chlorine at ambient temperature containing ratios of ethane to chlorine varying from about 0.94:1 to about 3.33:1, were fed to a preheated quartz tubular reactor 140 cm long and having an inner diameter of 8 cm. Reactions of ethane and chlorine were carried out at 625° C., 675° C., and 740° C., as determined from the exterior surface of the middle of the reactor (the so-called "mid-skin temperature"). Residence time in the reactor was about 4 seconds. The reaction product was air quenched and water cooled and, after equilibrium was established, analyzed by gas chromatography. The results were as follows.

TABLE I

| Yields of Ethylene, Vinyl Chloride and Ethyl Chloride As A Function of Temperature And Ethane/Chlorine Mole Ratio | | | | |
|---|---|---|---|---|
| Reactions Conditions | | Yield/% | | |
| Temp/ °C. | Ethane/Chlorine Mole Ratio | Ethylene | Vinyl Chloride | Ethyl Chloride |
| 740 | 1.08:1 | 72.4 | 13.7 | 0 |
|  | 1.61:1 | 84.4 | 7.3 | 0 |
|  | 2.43:1 | 88.1 | 3.2 | 0 |
|  | 3.21:1 | 88.5 | 2.5 | 0 |
| 675 | 1.04:1 | 67.0 | 24.6 | 3.3 |
|  | 1.68:1 | 78.9 | 13.3 | 4.8 |
|  | 2.48:1 | 82.4 | 9.4 | 4.6 |
|  | 3.31:1 | 80.6 | 6.7 | 9.5 |
| 625 | 0.94:1 | 62.1 | 28.5 | 5.5 |
|  | 1.65:1 | 53.3 | 15.2 | 30.1 |
|  | 2.61:1 | 46.0 | 8.1 | 43.0 |
| 3.33:1 |  | 44.4 | 6.7 | 47.2 |

Figure 1:
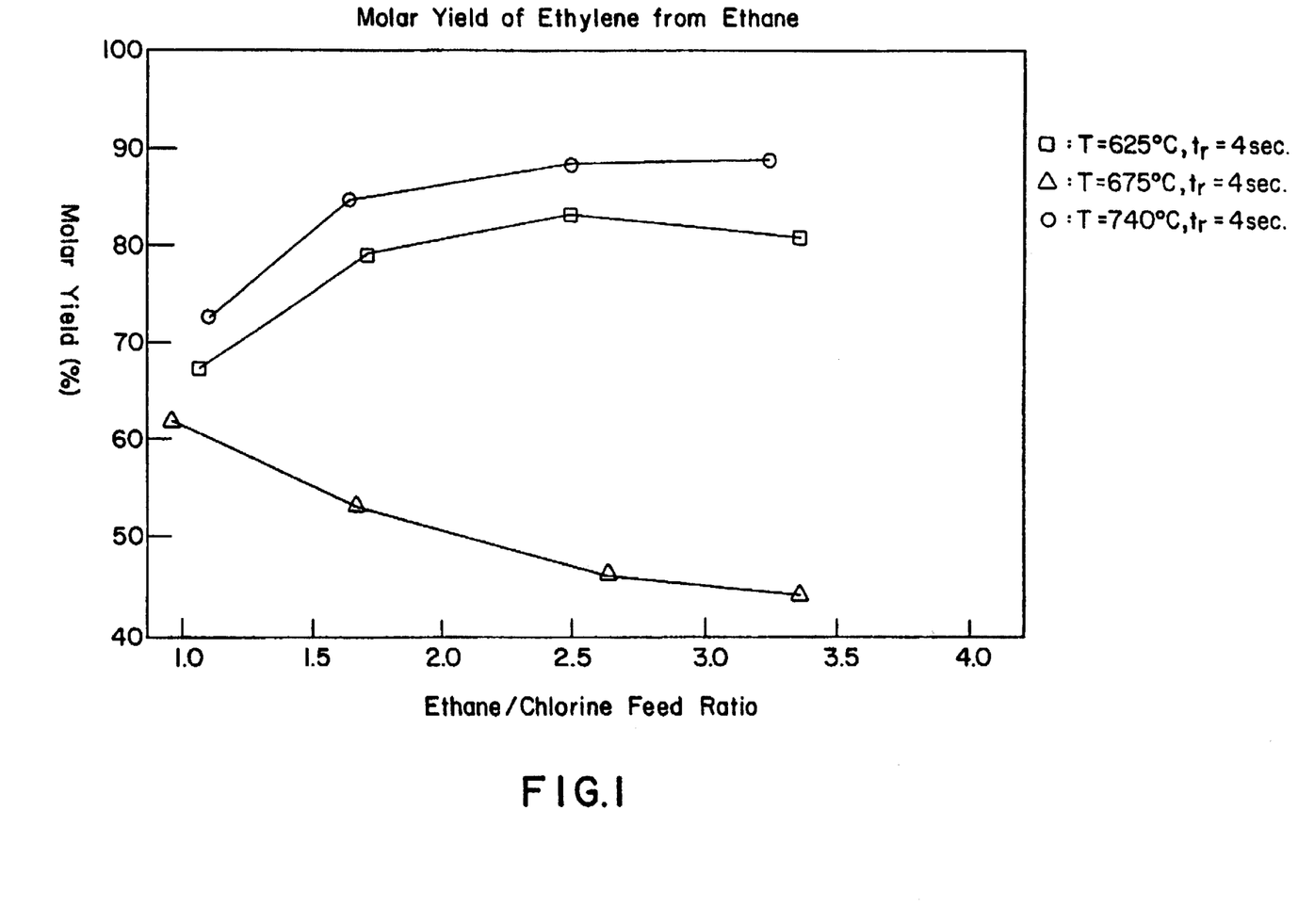
FIG. 1 is a graph showing the yield of ethylene in the process of this invention as a function of the ratio of ethane to chlorine in the feed and of the reaction temperature.
Figure 2:
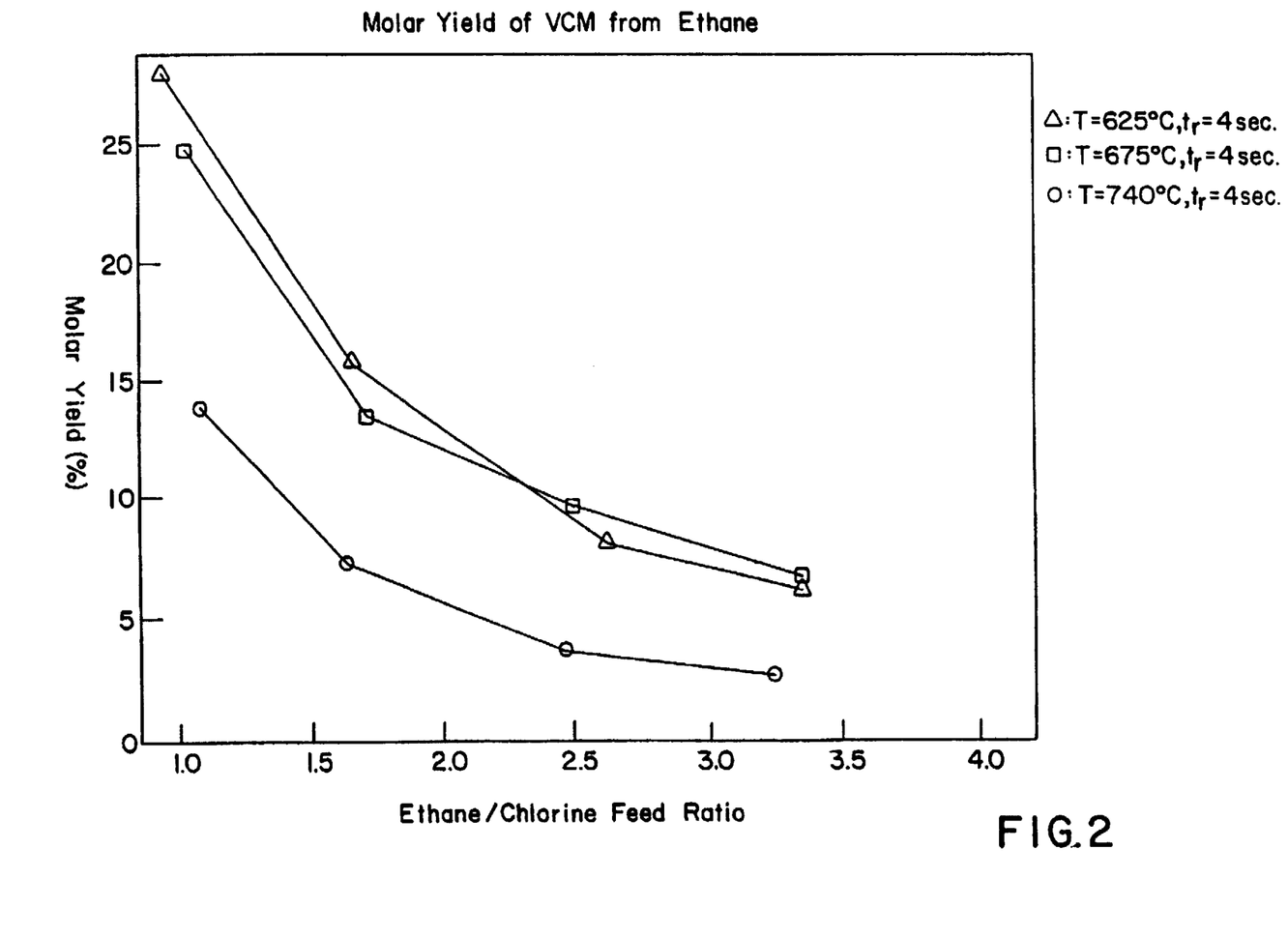
FIG. 2 is a graph showing the yield of vinyl chloride as a function of the ratio of ethane to chlorine in the feed and as a function of the reaction temperature.
Figure 3:
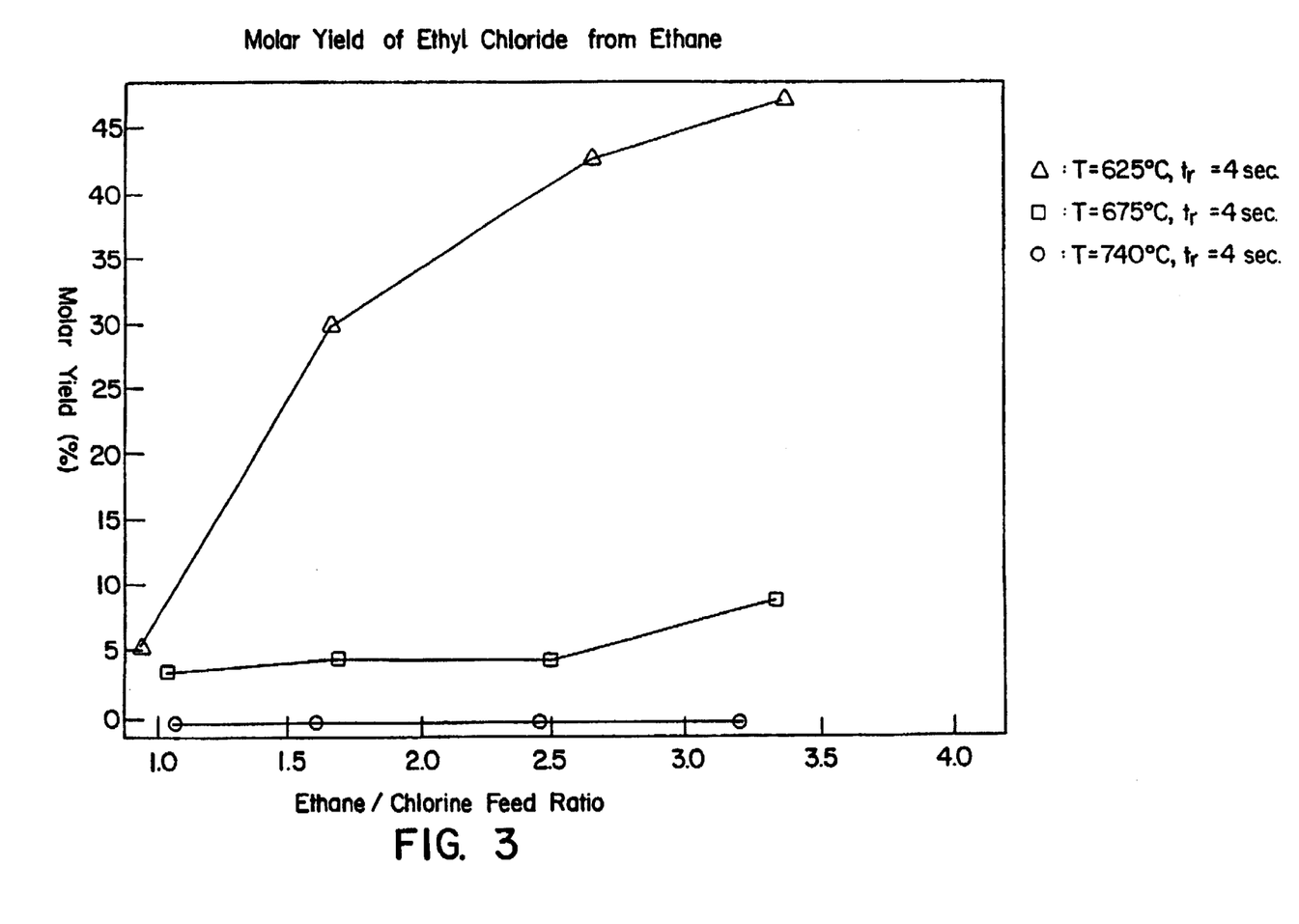
FIG. 3 is a graph showing the yield of ethyl chloride in the process of this invention as a function of the ratio of ethane to chlorine in the feed and as a function of the reaction temperature.

The yields of ethylene, vinyl chloride and ethyl chloride are plotted as a function of mole ratio and temperature in FIGS. 1, 2, and 3, respectively.

As can be seen from Table I and FIGS. 1–3, when the reaction temperature was above 650° C., the yield of vinyl chloride decreased with increasing ratio of ethane to chlorine in the feed. In addition, the yield of ethyl chloride increased as reaction temperature decreased and, at lower temperatures, also increased with increased ratio of ethane to chlorine in the feed. Consequently, at a temperature of 625° C., good yields of ethylene and vinyl chloride were obtained only at an ethane to chlorine ratio of about 1:1.

EXAMPLE 2

Employing the apparatus described in Example 1, a series of reactions was run at an ethane/chlorine feed ratio of 1.39:1 and a reactor temperature of 675° C., but retention time was varied from 3 to 11 seconds. Ethane consumption and yields of ethylene, vinyl chloride, and ethyl chloride were found to be as follows.

| | | Yields/% | | | |
|---|---|---|---|---|---|
| Reaction Time/Sec | Ethane Conversion/% | Ethylene | Vinyl Chloride | Ethylene +VCl | Ethyl Chloride |
| 2.9 | 69.8 | 71.7 | 17.3 | 89 | 6.6 |
| 3.7 | 69.8 | 72.3 | 17.9 | 90.2 | 5.9 |
| 7.3 | 70.5 | 79.5 | 16.2 | 95.7 | 0.2 |
| 11.0 | 68.8 | 79.5 | 15.7 | 95.2 | 0 |

Figure 4:
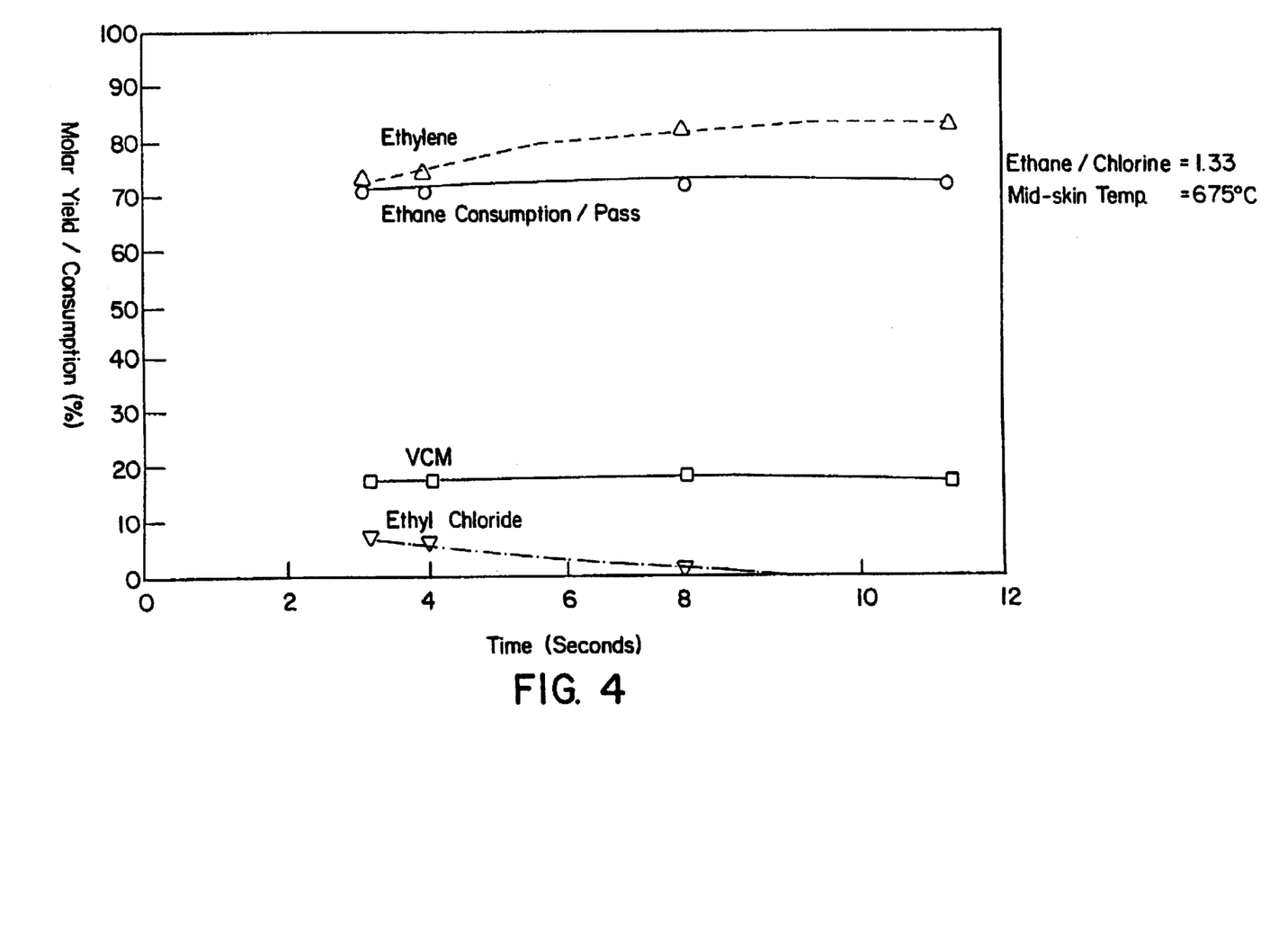
FIG. 4 is a graph showing ethane conversion, and yields of ethylene, vinyl chloride, and ethyl chloride, as a function of reaction time.

The dependence of ethane consumption and product yields is plotted as a function of reaction time in FIG. 4.

As is evident, increased reaction time increased the yield of ethylene and reduced the yield of ethyl chloride, but had no significant effect on ethane conversion or vinyl chloride yield.

Comparative Example A

This example was intended to duplicate the experimental conditions given in Example 1 of U.S. Pat. No. 2,259,195, with the exception that ethane was substituted for the butane used in the patent example. Sixty 1/hour of ethane and 120 1/hour of chlorine were premixed in a 2.2 mm ID Teflon tube which was 50 cm long. The mixture was passed through a 2 mm quartz capillary tube against a frontal perforated plate heated externally by an electric furnace. The resulting reaction mixture passed through an air cooled section and a water cooled exchanger. The frontal plate was arranged in a 15 mm inside diameter quartz tube. The skin temperature of the tube was measured. Reactor skin temperatures of 300°, 600°, and 800° C. were tested. At all temperatures tested, large amounts of carbon were formed. In fact, carbon formation was so severe that in every case the reaction tube was plugged with carbon less than a minute after gas flows were stabilized. Because of the short operation time, gas chromatographic analysis could not be performed to determine what other products, besides carbon, were formed in the reaction.

We claim:

1. A process for preparing ethylene or a mixture of ethylene and vinyl chloride by the reaction of ethane and chlorine which comprises:

(a) providing a stream of ethane feed gas and a stream of chlorine feed gas;

(b) thoroughly mixing said ethane and chlorine feed gases in a mixing zone at a molar ratio of ethane to chlorine of at least about 0.9;

(c) controlling the temperatures of said ethane feed gas and said chlorine feed gas so that substantially no chemical reaction takes place during and immediately after said mixing and so that the temperature of such mixture of gases immediately after mixing is less than about 215° C.;

(d) passing said mixture into an inert reaction zone;

(e) heating said mixture in said inert reaction zone to initiate chemical reaction between said ethane and said chlorine in the essential absence of a catalyst for this reaction;

(f) continuing the providing of heat to said reacting mixture as required so that the reacted mixture will have a temperature between about 600° C. and 800° C.; whereby the yield of ethylene is at least about 62.1% and combined molar yield of ethylene and vinyl chloride is at least about 80% of the ethane consumed.

2. A process according to claim 1 wherein said temperature is about ambient temperature.

3. A process according to claim 1 wherein said reacted mixture has a temperature between about 650° C. and about 750° C.

4. A process according to claim 1 wherein said molar ratio of ethane to chlorine is between about 1:1 to about 4:1.

5. A process according to claim 1 wherein said molar ratio of ethane to chlorine is between about 1:1 to about 2:1.

6. A process according to claim 1 wherein said molar ratio of ethane to chlorine is between about 1.3:1 to about 1.6:1.

7. A process according to claim 1 wherein said reaction between said ethane and said chlorine is substantially completed within about 1 minute after the commencement of said mixing.

8. A process according to claim 1 wherein said reaction between said ethane and said chlorine is substantially completed within about 10 seconds after the commencement of said mixing.

9. A process according to claim 1 wherein said ethane and said chlorine are reacted in an inert reaction zone made of a material selected from quartz, silicon carbide, alumina, and graphite.

10. A process according to claim 1 further comprising reacting the ethylene and hydrogen chloride produced from the reaction of ethane and chlorine with an oxygen source to produce dichloroethane.

11. A process according to claim 10 further comprising heating said dichloroethane to produce vinyl chloride.

12. A process according to claim 1 wherein the ethane converted per pass through said reactor is at least about 50% of the ethane in the feed.

13. A process for preparing ethylene or a mixture of ethylene and vinyl chloride by the reaction of ethane and chlorine which comprises:

(a) providing a stream of ethane feed gas and a stream of chlorine feed gas;

(b) thoroughly mixing said ethane and chlorine feed gases in a mixing zone at a molar ratio of ethane to chlorine of at least about 1.1:1 to about 1.9:1;

(c) controlling the temperatures of said ethane feed gas and said chlorine feed gas so that the temperature of such mixture of gases is ambient temperature and so that substantially no chemical reaction takes place during and immediately after said mixing;

(d) passing said mixture into an inert reaction zone;

(e) heating said mixture in said inert reaction zone to initiate chemical reaction between said ethane and said chlorine in the essential absence of a catalyst for this reaction and a diluent;

(f) continuing the providing of heat to said reacting mixture so that the reacted mixture will have a temperature between about 650° C. and about 750° C.;

whereby the yield of ethylene is at least about 62.1% and combined molar yield of ethylene and vinyl chloride is at least about 90% of the ethane consumed.

14. A process for preparing ethylene or a mixture of ethylene and vinyl chloride by the reaction of ethane and chlorine which comprises:

(a) providing a stream of ethane feed gas and a stream of chlorine feed gas;

(b) thoroughly mixing said ethane and chlorine feed gases in a mixing zone at a molar ratio of ethane to chlorine of at least about 0.9;

(c) controlling the temperatures of said ethane feed gas and said chlorine feed gas so that substantially no chemical reaction takes place during and immediately after said mixing and so that the temperature of such mixture of gases immediately after mixing is less than about 215° C.;

(d) passing said mixture into an inert reaction zone;

(e) heating said mixture in said inert reaction zone to initiate chemical reaction between said ethane and said chlorine in the essential absence of a catalyst for this reaction and a diluent;

(f) continuing the providing of heat to said reacting mixture as required so that the reacted mixture will have a temperature between about 600° C. and 800° C.;

whereby the yield of ethylene is at least about 62.1% and combined molar yield of ethylene and vinyl chloride is at least about 80% of the ethane consumed.

15. A process according to claim 13 wherein said molar ratio of ethane to chlorine is between about 1.3:1 to about 1.6:1.

16. A process according to claim 13 wherein said reaction between said ethane and said chlorine is substantially completed within about 1 minute after the commencement of said mixing.

17. A process according to claim 13 wherein said reaction between said ethane and said chlorine is substantially completed within about 10 seconds after the commencement of said mixing.

18. A process according to claim 13 wherein said ethane and said chlorine are reacted in an inert reaction zone made of a material selected from quartz, silicon carbide, alumina, and graphite.

19. A process according to claim 13 further comprising reacting ethylene and hydrogen chloride produced from the reaction of ethane and chlorine with an oxygen source to produce dichloroethane.

20. A process according to claim 13 further comprising heating said dichloroethane to produce vinyl chloride.

21. A process according to claim 13 wherein the ethane converted per pass through said reactor is at least about 50% of the ethane in the feed.

22. A process according to claim 14 wherein said reacted mixture has a temperature between about 650° C. and about 750° C.

23. A process according to claim 14 wherein said molar ratio of ethane to chlorine is between about 1:1 to about 4:1.

24. A process according to claim 14 wherein said molar ratio of ethane to chlorine is between about 1:1 to about 2:1.

25. A process according to claim 14 wherein said molar ratio of ethane to chlorine is between about 1.3:1 to about 1.6:1.

26. A process according to claim 14 wherein said reaction between said ethane and said chlorine is substantially completed within about 1 minute after the commencement of said mixing.

27. A process according to claim 14 wherein said reaction between said ethane and said chlorine is substantially completed within about 10 seconds after the commencement of said mixing.

28. A process according to clam 14 wherein said ethane and said chlorine are reacted in an inert reaction zone made of a material selected from quartz, silicon carbide, alumina, and graphite.

29. A process according claim 14 further comprising react the ethylene and hydrogen chloride produced from the reaction of ethane and chlorine with an oxygen source to produce dichloroethane.

30. A process according to claim 14 further comprising heating said dichloroethane to produce vinyl chloride.

31. A process according to claim 14 wherein the ethane converted per pass through said reactor is at least about 50% of the ethane in the feed.

* * * * *